US006812230B2

(12) United States Patent
Horuk

(10) Patent No.: US 6,812,230 B2
(45) Date of Patent: Nov. 2, 2004

(54) NON-PEPTIDE CCR1 RECEPTOR ANTAGONISTS FOR THE TREATMENT OF PROGRESSIVE RENAL FIBROSIS

(75) Inventor: Richard Horuk, Lafayette, CA (US)

(73) Assignee: Schering Aktiengesellschaft, Berlin (DE)

(*) Notice: Subject to any disclaimer, the term of this patent is extended or adjusted under 35 U.S.C. 154(b) by 5 days.

(21) Appl. No.: 10/205,713

(22) Filed: Jul. 26, 2002

(65) Prior Publication Data

US 2003/0109534 A1 Jun. 12, 2003

Related U.S. Application Data

(60) Provisional application No. 60/310,538, filed on Aug. 7, 2001.

(51) Int. Cl.[7] ................... A61K 31/495; A61K 31/496; A61K 31/5371; A61K 31/54; A61K 38/00

(52) U.S. Cl. .................. 514/255.01; 514/254.01; 514/254.02; 514/254.05; 514/254.8; 514/9

(58) Field of Search ................. 514/235.8, 252.11, 514/254.01, 254.02, 254.05, 254.08, 254.1, 255.01, 9

(56) References Cited

U.S. PATENT DOCUMENTS 6,207,665 B1    3/2001  Bauman et al.
6,555,537 B2 *  4/2003  Bauman et al. .......... 514/235.8
6,649,611 B2 * 11/2003  Blumberg et al. ....... 514/235.8

FOREIGN PATENT DOCUMENTS

WO    WO 98/56771 A2 * 12/1998    ......... C07D/241/00

OTHER PUBLICATIONS

"Airway Remodeling Is Absent in CCR1–/–Mice During Chronic Fungal Allergic Airway Disease", Blease et al., The journal of Immunology, 2000, 165:1564–1572.*
"Chemokines, Chemokine Receptors, and Renal Disease: From Basic Science to Pathophysiologic and Therapeutic Studies", Segerer et al., J Am Soc Nephrol, 11: 152–176, 2000.*
"Chemokines and Inflammatory Renal Diseases", Schwarz et al., Kidney Blood Press Res, 2001, 24:213–440.*
"Expression of Chemokines and Their Receptors in Nephrotoxic Serum Nephritis", Schadde et al., Nephro Dial Transplant, 2000, 15:1046–1053.*
"Pivotal Role of CCR1–Positive Leukocytes in Bleomycin–Induced Lung Fibrosis in Mice", Tokuda et al., The American Association of Immunologists, 2000, 164:2745–2751.*
Horuk, et al., "A Non–peptide Functional Antagonist of the CCR1 Chemokine Receptor Is Effective in Rat Heart Transplant Rejection", J. Biol. Chem., (2001) 276(6):4199–4204.
Liang et al., "Species selectivity of a small molecule antagonist for the CCR1 chemokine receptor", Eur. J. Phar., (2000) 389:41–49.
Liang et al., "Identification and Characterization of a Potent, Selective, and Orally Active Antagonist of the CC Chemokine Receptor–1", J. Biol. Chem., (2000) 275(25):19000–19008.

(List continued on next page.)

Primary Examiner—Vickie Kim
Assistant Examiner—Brian-Yong S. Kwon
(74) Attorney, Agent, or Firm—Neil G. Miyamoto

(57) ABSTRACT

This invention is directed to pharmaceutical compositions useful in treating progressive renal fibrosis in mammals comprising a pharmaceutically acceptable excipient and a therapeutically effective amount of a non-peptide CCR1 receptor antagonist.

4 Claims, 9 Drawing Sheets

OTHER PUBLICATIONS

Hesselgesser et al., "Identification and Characterization of Small Molecule Functional antagonists of the CCR1 Chemokine Receptor", *J. Biol. Chem.*, (1998) 273(25):15687–15692.

Ng et al., "Discovery of Novel Non–Peptide CCR1 Receptor Antagonists", *J. Med. Chem.*, (1999) 42:4680–4694.

Horuk et al., "CCR1 specific non–peptide antagonist: efficacy in a rabbit allograft rejection model", *Immunol. Lett.* (2001) 76(3):193–201.

Vielhauer et al., "Obstructive nephropathy in the mouse: progressive fibrosis correlates with tubulointerstitial chemokine expression and accumulation of CC chemokine receptor–2 and 5–positive leukocytes", *J. Amer. Soc. Nephrol.*, (2001) 12:1173–1187.

* cited by examiner

A

B

| 1 | 2 | 3 | 4 | 1 | 2 | 3 | 4 |
| UUO | | UUO | | CLK | | CLK | |
| BX 1-10d | | Vehicle | | BX 1-10d | | Vehicle | | ns
NON-PEPTIDE CCR1 RECEPTOR ANTAGONISTS FOR THE TREATMENT OF PROGRESSIVE RENAL FIBROSIS

This is a non-provisional application claiming priority under 35 U.S.C. § 119 provisional application Ser. No. 60/310,538, filed Aug. 7, 2001.

FIELD OF THE INVENTION

The present invention relates to pharmaceutical compositions useful in the treatment of progressive renal fibrosis in mammals which comprise a pharmaceutically acceptable excipient and a therapeutically effective amount of a non-peptide CCR1 receptor antagonist. The present invention also relates to a method of using such pharmaceutical compositions in treating progressive renal fibrosis in mammals.

BACKGROUND OF THE INVENTION

An important component of the inflammatory process involves the migration and activation of select populations of leukocytes from the circulation and their accumulation in the affected tissue. While the idea of leukocyte trafficking is not new, it has enjoyed a renaissance recently following the discovery and characterization of the selectin and integrin families of adhesion molecules and the large family of selective chemotactic cytokines known as chemokines. Chemokine receptors are expressed on leukocytes and process the signals following the binding of the chemokine whereby such signals are eventually transduced into migration or activation of the leukocytes towards the source of the chemokine. Therefore, by regulating the migration and activation of leukocytes from the peripheral blood to extravascular sites in organs, skin, articulations or connective, tissue, chemokines play a critical role in the maintenance of host defense as well as in the development of the immune response.

Originally, the chemokine family of molecules was divided into two groups: the "C—X—C" subfamily and the "C—C" subfamily. The characteristic feature of both of these subfamilies is the presence of four cysteine residues in highly conserved positions in the molecules. In the "C—C" chemokine subfamily, the first two residues are adjacent to each other, while in the "C—X—C" subfamily, a single amino acid residue separates the cysteine residues. A recent description of a "—C—" chemokine appears to represent a new family of chemokines in that the "—C" chemokine lacks two of the four cysteine residues present in the "C—C" subfamily or the "C—X—C" subfamily.

One member of the "C—C" subfamily of chemokines is macrophage inflammatory protein-1α ("MIP-1α"). It is expressed by cells such as macrophages, T and B lymphocytes, neutrophils and fibroblasts. A recent study (see Karpus, W. J. et al., J. Immunol. (1995), Vol. 155, pp. 5003–5010) provides strong in vivo concept validation for a role of MIP-1α in a mouse experimental autoimmune encephalomyelitis ("EAE") model of multiple sclerosis. Multiple sclerosis is an autoimmune disease mediated by T and B lymphocytes and macrophages, resulting in extensive inflammation and demyelination of white matter in the central nervous system. The study showed that antibodies to MIP-1α prevented the development of both initial and relapsing disease as well as preventing the infiltration of mononuclear cells into the central nervous system. Treatment with the antibodies was also able to ameliorate the severity of ongoing clinical disease. These results led the investigators to conclude that MIP-1α plays an important role in the etiology of multiple sclerosis. Another study (see Godiska, R. et al., J. Neuroimmunol. (1995), Vol. 58, pp. 167–176) demonstrated the upregulation of mRNA for a number of chemokines, including MIP-1α in the lesions and spinal cord of SJL mice (a strain of mice susceptible to $Th_1$ diseases such as EAE) during the course of acute EAE.

RANTES is another member of the C—C chemokine subfamily (the name RANTES is an acronym derived from some of the original observed and predicted characteristics of the protein and its gene: Regulated upon Activation Normal T cell Expressed presumed Secreted). A wide variety of tissues have been found to express RANTES in a similar pattern to MIP-1α. There is evidence from a number of studies to implicate the abnormal production of RANTES in the progression of rheumatoid arthritis (see Rathanaswami, P. et al., J. Biol. Chem. (1993), Vol. 268, pp. 5834–5839 and Snowden, N. et al., Lancet (1994), Vol. 343, pp. 547–548). Rheumatoid arthritis is a chronic inflammatory disease characterized in part by a memory T lymphocyte and monocyte infiltration, which is believed to be mediated by chemotactic factors released by inflamed tissues. There is strong evidence from other studies implicating RANTES in the pathophysiology of rheumatoid arthritis (see Barnes, D. A. et al., J. Clin. Invest. (1998), Vol. 101, pp. 2910–2919 and Plater-Zyberk, C. A. et al., Immunol. Lett. (1997), Vol.57, pp.117–120). For example, in a rat adjuvant-induced arthritis ("AIA") model, antibodies to RANTES greatly reduced the development of disease.

These studies and others provide strong evidence that MIP-1α levels are increased in EAE models of multiple sclerosis and that RANTES levels are increased in rheumatoid arthritis (see, e.g., Glabinski, A. R. et al., Am. J. Pathol. (1997), Vol. 150, pp. 617–630; Glabinski, A. R. et al., Methods Enzymol. (1997), Vol. 288, pp. 182–190; and Miyagishi, R. S. et al., J. Neuroimmunol. (1997), Vol. 77, pp. 17–26). In addition, as described above, these chemokines are chemoattractants for T cells and monocytes, which are the major cell types that are involved in the pathophysiology of these diseases. Therefore, any molecule that inhibits the activity of either of these chemokines would be beneficial in treating these diseases and would therefore be useful as an anti-inflammatory agent.

There is also evidence linking MIP-1α and RANTES to progressive renal fibrosis, which is the main predictor for the progression to end-stage renal disease and is characterized by a mixed tubulointerstitial leukocytic cell infiltration, fibroblast proliferation, and increased extracellular matrix production leading to tubular cell necrosis and apoptosis (see Becker, G. J. and Hewitson, T. D., Curr. Opin. Nephrol. Hypertens. (2000), Vol. 9, pp. 133–138; Harris, D. C. H., Curr. Opin. Nephrol. Hypertens. (2001), Vol. 10, pp. 303–313; and Zeisberg, M. et al., Curr. Opin. Nephrol. Hypertens. (2001), Vol. 10, pp. 315–320). During this process, infiltrating macrophages and lymphocytes are a major source of inflammatory mediators such as cytokines, nitric oxide, growth factors, and reactive oxygen species. Inhibition of leukocyte infiltration may reduce the production of such inflammatory mediators and, hence, may be a therapeutic option to halt progressive renal fibrosis and to prevent or delay end-stage renal disease.

Leukocyte infiltration is triggered by locally secreted chemokines. In a widely used mouse model for progressive renal fibrosis that is independent of hypertension or systemic immune disease, unilateral ureteral obstruction ("UUO"), the expression of MIP-1α, RANTES and MIP-1β is increased in parallel with the progression of renal fibrosis (see Vielhauer, V. et al., *J. Amer. Soc. Nephrol.* (2001), Vol. 12, pp. 1173–1187). Since MIP-1α and RANTES are ligands for the "C—C" chemokine receptors CCR1 and CCR5, then these receptors, located on circulating mononuclear cells, may be useful therapeutic targets in progressive renal fibrosis. After UUO, the expression of the CCR1 receptor increases in parallel with its ligands (Vielhauer, V. et al., (2001), supra). Since the CCR1 receptor is known to mediate the migration of mononuclear cells into inflamed tissue, any molecule that inhibits its activity would be beneficial in treating progressive renal fibrosis.

Certain small molecules have recently been shown to be non-peptide CCR1 receptor antagonists by inhibiting the activity of RANTES and MIP-1α and are therefore useful as anti-inflammatory agents. See PCT Published Patent Application WO 98/56771; U.S. patent application, Ser. No. 09/094,397, filed Jun. 9, 1998, now U.S. Pat. No. 6,207,665, issued Mar. 27, 2001; Hesselgesser, J. et al., *J. Biol. Chem.* (1998), Vol. 273, pp. 15687–15692; Ng, H. P. et al., *J. Med. Chem.* (1999), Vol. 42, pp. 46804694; Liang, M. et al., *Eur. J. Pharmacol.* (2000a), Vol. 389, pp. 41–49; Liang, M. et al., *J. Biol. Chem.* (2000b), Vol. 275, pp. 19000–19008; Horuk, R. et al., *J. Biol. Chem.* (2001a), Vol. 276, pp. 4199–4204; and Horuk, R. et al., *Immunol. Lett.* (2001b), Vol. 76, pp. 193–201. The disclosures of these patent applications and journal articles are incorporated in full by reference herein.

SUMMARY OF THE INVENTION

This invention is directed to pharmaceutical compositions useful in treating progressive renal fibrosis in mammals, which compositions comprise a pharmaceutically acceptable excipient and a therapeutically effective amount of a non-peptide CCR1 receptor antagonist. In particular, this invention is directed to pharmaceutical compositions useful in treating progressive renal fibrosis in mammals, which compositions comprise a pharmaceutically acceptable excipient and a therapeutically effective amount of a non-peptide CCR1 receptor antagonist selected from the compounds disclosed in U.S. Pat. No. 6,207,665.

This invention is also directed to methods of administering to a mammal in need thereof a pharmaceutical composition useful in treating progressive renal fibrosis in mammals, which composition comprises a pharmaceutically acceptable excipient and a therapeutically effective amount of a non-peptide CCR1 receptor antagonist. In particular, this invention is directed to methods of administering to a mammal in need thereof a pharmaceutical composition useful in treating progressive renal fibrosis in mammals, which composition comprises a pharmaceutically acceptable excipient and a therapeutically effective amount of a non-peptide CCR1 receptor antagonist selected from the compounds disclosed in U.S. Pat. No. 6,207,665.

This invention is also directed to methods of treating progressive renal fibrosis in a mammal which method comprises administering to a mammal in need thereof a pharmaceutical composition comprising a pharmaceutically acceptable excipient and a therapeutically effective amount of a non-peptide CCR1 receptor antagonist. In particular, this invention is directed to methods of treating progressive renal fibrosis in a mammal which method comprises administering to a mammal in need thereof a pharmaceutical composition comprising a pharmaceutically acceptable excipient and a therapeutically effective amount of a non-peptide CCR1 receptor antagonist selected from the compounds disclosed in U.S. Pat. No. 6,207,665.

DETAILED DESCRIPTION OF THE INVENTION

A. Definitions

Figure 1:
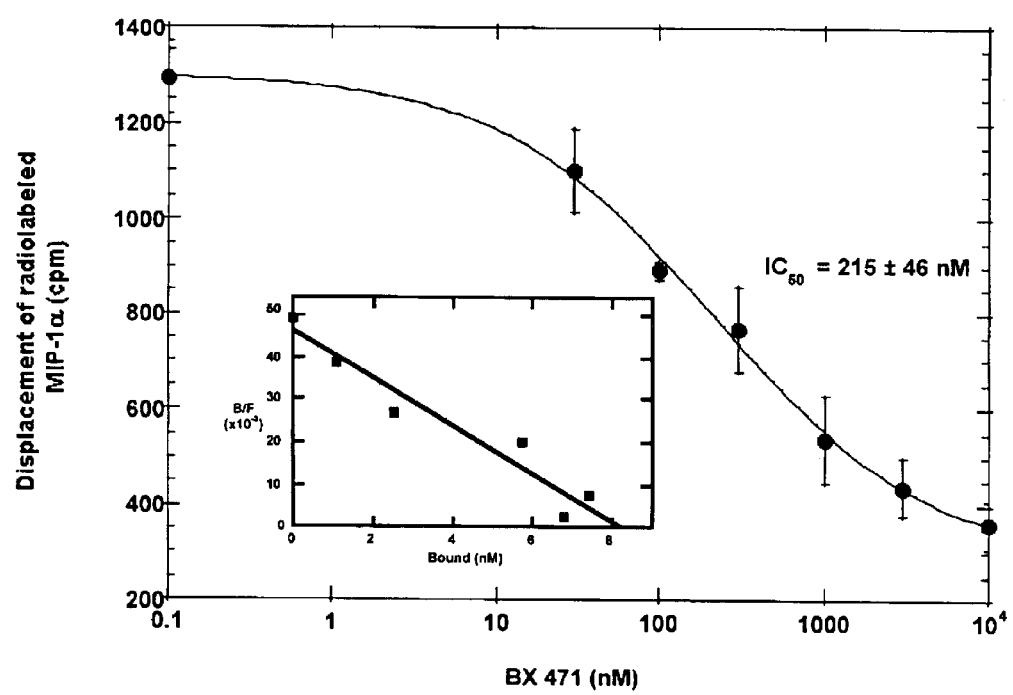
FIG. 1 shows the effect of a non-peptide CCR1 receptor antagonist of the invention on the binding of radiolabeled MIP-1α to mouse CCR1 expressing cells.

As used in the specification and appended claims, unless specified to the contrary, the following terms have the meaning indicated:

"Aminocarbonyl" refers to the radical —C(O)NH$_2$.

"Phenyl" refers to the benzene radical optionally substituted by one or more substituents selected from the group consisting of hydroxy, halo, alkyl, haloalkyl, alkoxy, alkenyl, nitro, cyano, amino, monoalkylamino, dialkylamino, alkylcarbonyl, carboxy, alkoxycarbonyl, and aminocarbonyl.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, zinc, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Ureido" refers to a radical of the formula —N(H)—C(O)—NH$_2$.

It is understood from the above definitions and examples that for radicals containing a substituted alkyl group any substitution thereon can occur on any carbon of the alkyl group.

"Mammal" includes humans and domesticated animals, such as cats, dogs, swine, cattle, sheep, goats, horses, rabbits, and the like.

"Progressive renal fibrosis" refers to those disease-states, for the purposes of this invention, which are: characterized by the expansion of the renal interstitium by a combination of events, including widened tubular cell basement membranes, infiltration of leukocytes and cells of the fibroblastic lineage, and gradual displacement of the interstitial areas with fibrous tissue; and associated with local tubular degeneration and dilatation.

The non-peptide CCR1 receptor antagonists of the invention may have asymmetric carbon atoms in their structure. The non-peptide CCR1 receptor antagonists may therefore exist as single stereoisomers, racemates, and as mixtures of enantiomers and diastereomers. All such single stereoisomers, racemates and mixtures thereof are intended to be within the scope of this invention. Absolute configuration of certain carbon atoms within the non-peptide CCR1 receptor antagonists, if known, is indicated by the appropriate absolute descriptor R or S. The descriptor "trans" is used to indicate that the R$^{1a}$ substituents are on opposite sides of the piperazine plane. The descriptor "cis" is used to indicate that the R$^{1a}$ substituents are on the same side of the piperazine plane.

The nomenclature for the non-peptide CCR1 receptor antagonists of the invention used herein is a modified form of the I.U.P.A.C. system wherein the non-peptide CCR1 receptor antagonists contemplated to be within the invention are named as piperazine derivatives, as described in U.S. Pat. No. 6,207,665.

"Therapeutically effective amount" refers to that amount of a non-peptide CCR1 receptor antagonist, preferably a non-peptide CCR1 receptor antagonist of formula (I) as described below, which, when administered to a mammal in need thereof, preferably a human, is sufficient to effect treatment, as defined below, for progressive renal fibrosis. The amount of non-peptide CCR1 receptor antagonist of the invention which constitutes a "therapeutically effective amount" will vary depending on the non-peptide CCR1 receptor antagonist utilized, the severity of the rejection, and the age of the human to be treated, but can be determined routinely by one of ordinary skill in the art having regard to his own knowledge and to this disclosure.

"Treating" or "treatment" as used herein covers the treatment of progressive renal fibrosis in a mammal, preferably a human, and includes:
(i) preventing the condition from occurring in a mammal, preferably a human, in particular, subsequent to an injury to the kidney in such mammal;
(ii) inhibiting the condition, i.e., arresting development of the progressive renal fibrosis; or
(iii) relieving the condition, i.e., causing regression of the progressive renal fibrosis.

B. Preferred Embodiments

Of the pharmaceutical compositions described above in the Summary of the Invention, a preferred group of pharmaceutical compositions include those compositions wherein the non-peptide CCR1 receptor antagonist is a compound selected from formula (I):

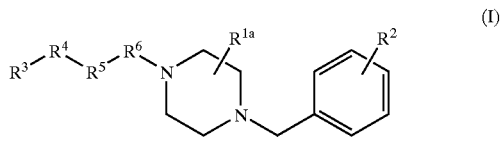

(I)

wherein:
R$^{1a}$ is one or more substituents independently selected from the group consisting of alkyl or hydroxyalkyl;
R$^2$ is fluoro at the 4-position;
R$^3$ is phenyl substituted at the 4-position with chloro and at the 2-position by aminocarbonyl, ureido or glycinamido;
R$^4$ is —O—;
R$^5$ is methylene; and
R$^6$ is —C(O)—;
as a single stereoisomer or a mixture thereof; or a pharmaceutically acceptable salt thereof.

Of this group of pharmaceutical compositions, a preferred subgroup of pharmaceutical compositions include those compositions wherein the non-peptide CCR1 receptor antagonist is selected from the group consisting of:

(2R,5S)-1-((4-chloro-2-(aminocarbonyl)phenoxy)methyl)carbonyl-2,5-dimethyl-4-(4-fluorobenzyl)piperazine;
(trans)-1-((4-chloro-2-(glycinamido)phenoxy)methyl)carbonyl-2,5-dimethyl-4-(4-fluorobenzyl)piperazine;
(2R)-1-((4-chloro-2-(ureido)phenoxy)methyl)carbonyl-2-methyl-4-(4-fluorobenzyl)piperazine;
(trans)-1-((4-chloro-2-(ureido)phenoxy)methyl)carbonyl-2,5-dimethyl-4-(4-fluorobenzyl)piperazine;
(2R,5S)-1-((4-chloro-2-(ureido)phenoxy)methyl)carbonyl-2,5-dimethyl-4-(4-fluorobenzyl)piperazine; and
(2R,5S)-1-((4-chloro-2-(glycinamido)phenoxy)methyl)carbonyl-2,5-dimethyl-4-(4-fluorobenzyl)piperazine.

Of this group of pharmaceutical compositions, another preferred subgroup of pharmaceutical compositions include those compositions wherein the non-peptide CCR1 receptor antagonist is (2R)-1-((4-chloro-2-(ureido)phenoxy)methyl)carbonyl-2-methyl-4-(4-fluorobenzyl)piperazine.

Of this subgroup of pharmaceutical compositions, a preferred class of pharmaceutical compositions include those compositions wherein the mammal in need thereof is a human.

Of the methods of administration as described above in the Summary of the Invention, a preferred group of methods include those methods wherein the non-peptide CCR1 receptor antagonist is administered to the mammal in need thereof.

Of this group of methods, a preferred subgroup of methods include those methods wherein the non-peptide CCR1 receptor antagonist is a compound selected from formula (I):

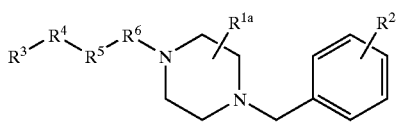

wherein:

$R^{1a}$ is one or more substituents independently selected from the group consisting of alkyl or hydroxyalkyl;
$R^2$ is fluoro at the 4-position;
$R^3$ is phenyl substituted at the 4-position with chloro and at the 2-position by aminocarbonyl, ureido or glycinamido;
$R^4$ is —O—;
$R^5$ is methylene; and
$R^6$ is —C(O)—;

as a single stereoisomer or a mixture thereof; or a pharmaceutically acceptable salt thereof.

Of this subgroup of methods, a preferred class of methods include those wherein the non-peptide CCR1 receptor antagonist is selected from the group consisting of:

(2R,5S)-1-((4-chloro-2-(aminocarbonyl)phenoxy)methyl)carbonyl-2,5-dimethyl-4-(4-fluorobenzyl)piperazine;
(trans)-1-((4-chloro-2-(glycinamido)phenoxy)methyl)carbonyl-2,5-dimethyl-4-(4-fluorobenzyl)piperazine;
(2R)-1-((4-chloro-2-(ureido)phenoxy)methyl)carbonyl-2-methyl4-(4-fluorobenzyl)piperazine;
(trans)-1-((4-chloro-2-(ureido)phenoxy)methyl)carbonyl-2,5-dimethyl-4-(4-fluorobenzyl)piperazine;
(2R,5S)-1-((4-chloro-2-(ureido)phenoxy)methyl)carbonyl-2,5-dimethyl-4-(4-fluorobenzyl)piperazine; and
(2R,5S)-1-((4-chloro-2-(glycinamido)phenoxy)methyl)carbonyl-2,5-dimethyl-4-(4-fluorobenzyl)piperazine.

Of this subgroup of methods, another preferred class of methods include those methods wherein the non-peptide CCR1 receptor antagonist is (2R)-1-((4-chloro-2-(ureido)phenoxy)methyl)carbonyl-2-methyl-4-(4-fluorobenzyl)piperazine.

Of this class of methods, a preferred subclass of methods include those methods wherein the mammal in need thereof is a human.

Of the methods of treatment described above in the Summary of the Invention, a preferred group of methods include those methods wherein the non-peptide CCR1 receptor antagonist is a compound selected from formula (I):

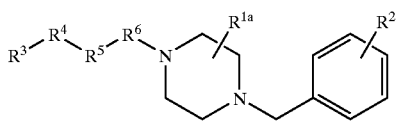

wherein:

$R^{1a}$ is one or more substituents independently selected from the group consisting of alkyl or hydroxyalkyl;
$R^2$ is fluoro at the 4-position;
$R^3$ is phenyl substituted at the 4-position with chloro and at the 2-position by aminocarbonyl, ureido or glycinamido;
$R^4$ is —O—;
$R^5$ is methylene; and
$R^6$ is —C(O)—;

as a single stereoisomer or a mixture thereof; or a pharmaceutically acceptable salt thereof.

Of this group of methods, a preferred subgroup of methods include those methods wherein the non-peptide CCR1 receptor antagonist is selected from the group consisting of:

(2R,5S)-1-((4-chloro-2-(aminocarbonyl)phenoxy)methyl)carbonyl-2,5-dimethyl-4-(4-fluorobenzyl)piperazine;
(trans)-1-((4-chloro-2-(glycinamido)phenoxy)methyl)carbonyl-2,5-dimethyl-4-(4-fluorobenzyl)piperazine;
(2R)-1-((4-chloro-2-(ureido)phenoxy)methyl)carbonyl-2-methyl-4-(4-fluorobenzyl)piperazine;
(trans)-1-((4-chloro-2-(ureido)phenoxy)methyl)carbonyl-2,5-dimethyl-4-(4-fluorobenzyl)piperazine;
(2R,5S)-1-((4-chloro-2-(ureido)phenoxy)methyl)carbonyl-2,5-dimethyl-4-(4-fluorobenzyl)piperazine; and
(2R,5S)-1-((4-chloro-2-(glycinamido)phenoxy)methyl)carbonyl-2,5-dimethyl-4-(4-fluorobenzyl)piperazine.

Of this group of methods, another preferred subgroup of methods include those methods wherein the non-peptide CCR1 receptor antagonist is (2R)-1-((4-chloro-2-(ureido)phenoxy)methyl)carbonyl-2-methyl-4-(4-fluorobenzyl)piperazine.

Of this subgroup of methods, a preferred class of methods include those methods wherein the mammal in need thereof is a human.

Of this subgroup of methods, another preferred class of methods includes those methods wherein the non-peptide CCR1 receptor antagonist is administered to the mammal in need thereof.

C. Utility of the Compositions of the Invention

The pharmaceutical compositions disclosed herein are useful for treating progressive renal fibrosis in mammals, preferably humans.

There is increasing evidence from human renal biopsy studies that the tubulointerstitial infiltration of leukocytes via the expression of certain chemokine receptors plays an important role in the progression of renal disease (see Segerer, S. et al., *J. Am. Soc. Nephrol.* (2000), Vol. 11, pp. 152–176; Segerer, S. et al., *Am. J. Kidney Dis.* (2001), Vol. 37, pp. 518–531; Furiuchi, K. et al., *Am J. Nephrol.* (2000), Vol. 20, pp. 291–299; and Grandaliano, G. et al., *Kidney Int.* (2000), Vol. 58, pp. 182–192). As described above, it has been shown that expression of the CCR1 receptor and two of its ligands, MIP-1α and RANTES, parallels the progression of renal fibrosis after UUO, a widely used animal model for progressive renal fibrosis (Vielhauer, V. et al., (2001), supra).

Based on these studies, there is evidence to support the theory that MIP-1α and RANTES, acting through the CCR1 receptor, play an important role in progressive renal fibrosis. The non-peptide CCR1 receptor antagonists of the invention have been shown to inhibit the activity of MIP-1α and RANTES. Therefore, the non-peptide CCR1 receptor antagonists of the invention are useful in treating progressive renal fibrosis.

As discussed in more detail below, the non-peptide CCR1 receptor antagonists of the invention substantially reduces interstitial cell infiltration and progressive renal fibrosis after UUO in mice. In particular, a therapeutically effective amount of a non-peptide CCR1 receptor antagonist demonstrates the ability to treat progressive renal fibrosis.

D. Testing of the Compounds of the Invention

To demonstrate that the non-peptide CCR1 receptor antagonists of the invention inhibit the activity of the chemokines MIP-1α or RANTES acting through the CCR1 receptor several in vitro assays may be employed that have been previously described. See, e.g., U.S. Pat. No. 6,207,665 and Hesselgesser, J. et al., (1998), supra, Ng, H. P. et al., (1999), supra, Liang, M. et al., (2000a), supra, and Liang, M. et al., (2000b), supra.

Figure 2:
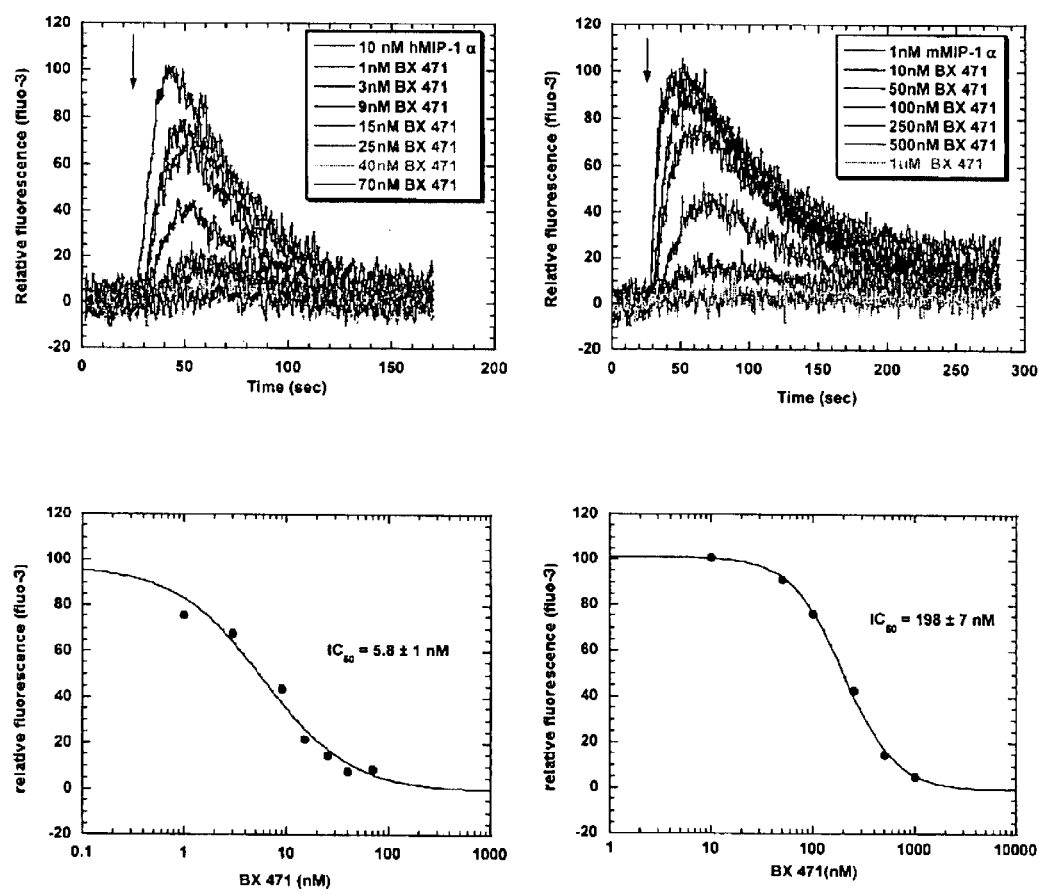
FIG. 2 shows the effect of a non-peptide CCR1 receptor antagonist of the invention on the MIP-1α induced rise in intracellular $Ca^{2+}$ in human and mouse CCR1 expressing cells.

A non-peptide CCR1 receptor antagonist disclosed in U.S. Pat. No. 6,207,665, i.e., (2R)-1-((4-chloro-2-(ureido)phenoxy)methyl)carbonyl-2-methyl-4-(4-fluorobenzyl)piperazine ("BX471"), was tested for binding to the mouse CCR1 receptor by in vitro binding assays, as described in Example 1, the results of which are illustrated in FIG. 1. Scatchard analysis of displacement binding studies revealed that the non-peptide CCR1 receptor antagonist BX471 was able to displace $^{125}$I-MIP-1α binding to the mouse CCR1 receptor with a $K_i$ of 215±46 nM (see FIG. 1). In competition binding studies, BX471 was able to displace $^{125}$I-MIP-1α binding to the human CCR1 receptor with a $K_i$ of 1±0.3 nM (see Liang, M. et al., (2000b), supra). The same non-peptide CCR1 receptor antagonist was shown to be a functional in vitro antagonist of the mouse CCR1 receptor by performing calcium flux assays as described below in Example 2, the results of which are illustrated in FIG. 2. The transient rise in intracellular $Ca^{2++}$ concentration induced by 10 nM human MIP-1α was inhibited by pre-incubating the human CCR1 receptor expressing cells with 1–70 nM of the non-peptide CCR1 receptor antagonist BX471 (see FIG. 2, left). The $IC_{50}$ for inhibition of the human CCR1 receptor was determined to be 5.8±1 nM. The transient rise in intracellular $Ca^{2++}$ concentration induced by 1 nM mouse MIP-1α was inhibited by pre-incubating mouse CCR1 receptor expressing cells with 10–1000 nM of the non-peptide CCR1 receptor antagonist BX471 (see FIG. 2, right). The $IC_{50}$ for inhibition of the mouse CCR1 receptor was determined to be 198±7 nM. These data demonstrated that although the non-peptide CCR1 receptor antagonist was not as potent an inhibitor of the mouse CCR1 receptor as compared to the human CCR1 receptor, the non-peptide CCR1 receptor antagonist competed effectively for binding to, and was a potent functional antagonist of, the mouse CCR1 receptor in vitro.

Figure 3:
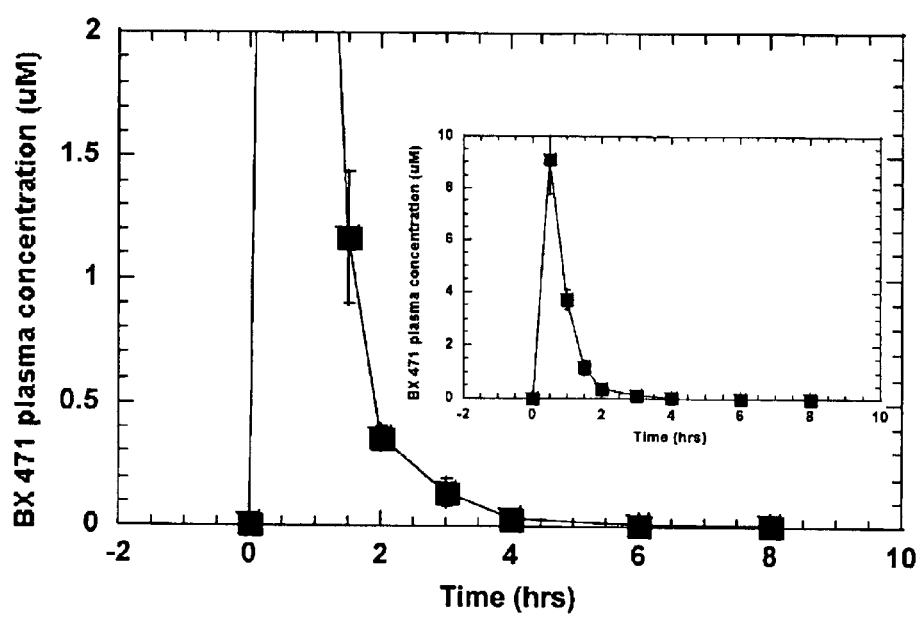
FIG. 3 shows the plasma concentrations of a non-peptide CCR1 receptor antagonist of the invention following subcutaneous administration in mice.

A pharmacokinetic study was carried out in mice with a non-peptide CCR1 receptor antagonist of the invention, as described below in Example 3, the results of which are illustrated in FIG. 3. After a single subcutaneous administration of 20 mg/kg of the non-peptide CCR1 receptor antagonist BX471, plasma samples were prepared and compound concentrations in the plasma were determined by HPLC-MS (see FIG. 3). BX471 reached peak plasma levels of ~9 μM by 30 minutes, and this level rapidly declined to ~0.4 μM after 2 hours. By 4 to 8 hours, BX471 plasma levels dropped to less than 0.1 μM. This study indicated that subcutaneous dosing of a non-peptide CCR1 receptor antagonist of the invention at 20 mg/kg three times per day would provide adequate drug levels over a 24-hour period.

An in vivo assay that may be employed to demonstrate the usefulness of the pharmaceutical compositions of the invention in treating progressive renal fibrosis in mammals is the mouse UUO model (see, e.g., Diamond, J. R. et al., Semin. Nephrol. (1998), Vol. 18, pp. 594–602, and Hruska, K. A. et al., Am. J. Physiol. Renal Physiol. (2000), Vol. 280, pp. F130–F143). The pharmaceutical compositions of the invention were tested in this in vivo assay, as described below in Example 4. The infiltration of leukocytes and the accumulation of activated fibroblasts in the peritubular interstitium of obstructed kidneys were characterized by immunohistochemistry of cortical renal sections, as described below in Example 5, the results of which are illustrated in FIG. 5 and quantified in FIG. 4. In this model, $CD45^+$ leukocytes, a cellular marker of inflammation, accumulated in the peritubular interstitium in the obstructed kidneys 6 days after UUO, and further increased in number 10 days after UUO (panels A and B in FIG. 5). There was a prominent infiltrate of $CD45^+$ leukocytes, $CD3^+$ lymphocytes and $F4/80^+$ macrophages in the peritubular interstitium 10 days after UUO, which was observed in the obstructed kidney (black bars), but not in the unobstructed contralateral kidney (white bars) ("Vehicle" in FIG. 4). In this model, activated $FSP-1^+$ fibroblasts, a cellular marker of fibrosis, accumulated in the peritubular interstitium in the obstructed kidneys in areas of marked tubular dilatation 6 days after UUO, and further increased in number 10 days after UUO (panel E ($FSP-1^+$ fibroblasts) in FIG. 5). The accumulation of $FSP-1^+$ fibroblasts was observed in the obstructed kidney (black bars), but not in the unobstructed contralateral kidney (white bars) ("Vehicle" in FIG. 4). These data demonstrated that leukocyte infiltration and renal fibrosis were readily detectable in the peritubular interstitium in the obstructed kidneys 6 days after UUO, and further increased 10 days after UUO.

Figure 4:
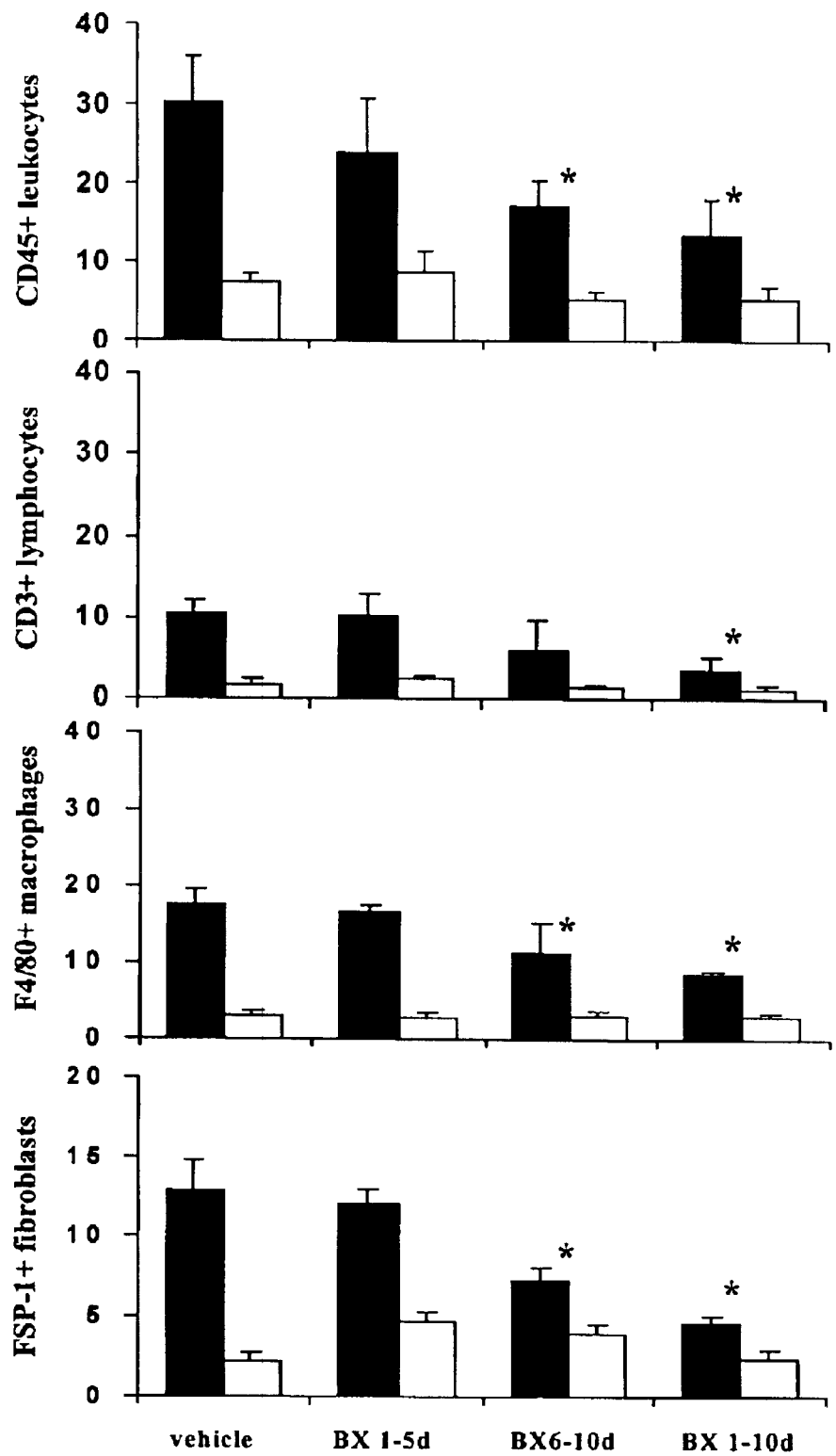
FIG. 4 shows the effect of a non-peptide CCR1 receptor antagonist of the invention on the infiltration of leukocytes and accumulation of activated fibroblasts in the peritubular interstitium of mice after unilateral ureteral obstruction (quantitative analysis).
Figure 5:
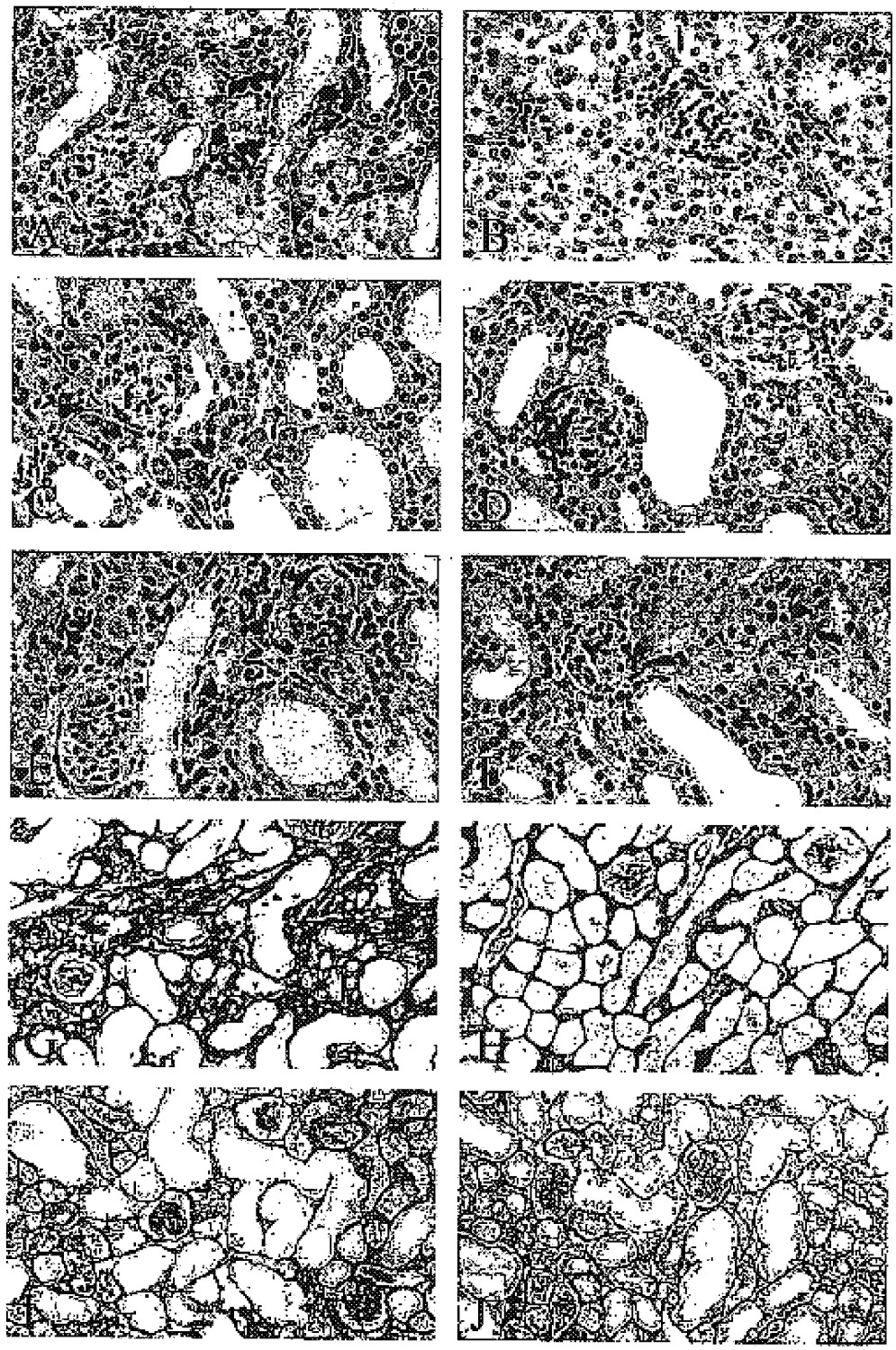
FIG. 5 shows the effect of a non-peptide CCR1 receptor antagonist of the invention on the infiltration of leukocytes and accumulation of activated fibroblasts in the peritubular interstitium of mice after unilateral ureteral obstruction (histology).

The mean number of infiltrating leukocytes and activated fibroblasts in the peritubular interstitium in the obstructed kidneys was significantly decreased in those animals given 20 mg/kg three times per day of the non-peptide CCR1 receptor antagonist, i.e. (2R)-1-((4chloro-2-(ureido)phenoxy)methyl)carbonyl-2-methyl-4-(4-fluorobenzyl)piperazine ("BX") for 10 days following UUO ("BX 1–10 d") in FIG. 4; and panels D ($CD45^+$ leukocytes) and F ($FSP-1^+$ fibroblasts) in FIG. 5) or for 5 days from days 6–10 following UUO ("BX 6–10 d" in FIG. 4; and panel C ($CD45^+$ leukocytes) in FIG. 5). There was no significant decrease in the number of infiltrating leukocytes or activated fibroblasts in the obstructed kidneys of animals treated with the non-peptide CCR1 receptor antagonist for 5 days from days 1–5 following UUO ("BX 1–5 d" in FIG. 4). This data demonstrated that the non-peptide CCR1 receptor antagonist was able to substantially reduce interstitial leukocyte infiltration and fibroblast accumulation in the obstructed kidneys when given to animals for 10 days immediately following UUO or 5 days from days 6–10 following UUO.

Figure 6:
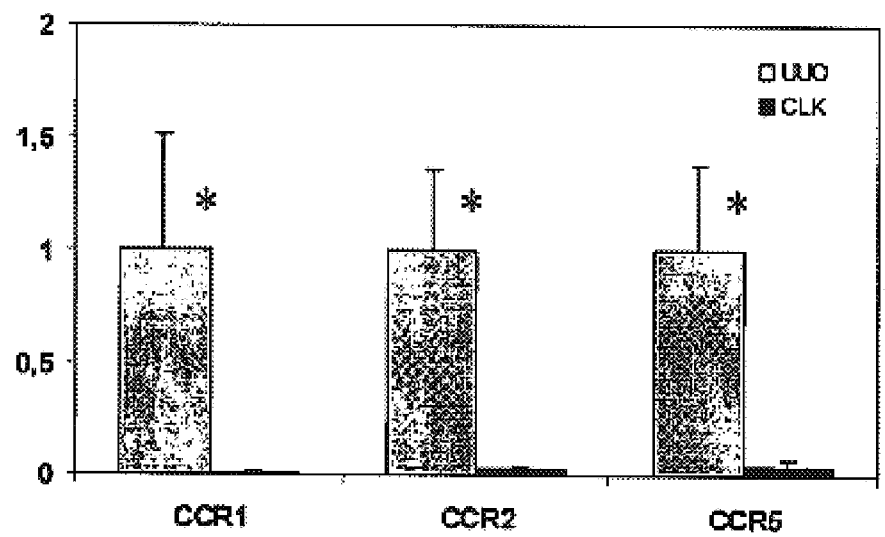
FIG. 6 shows the effect of a non-peptide CCR1 receptor antagonist of the invention on the expression of chemokine receptors on renal cells of mice after unilateral ureteral obstruction.
Figure 6:
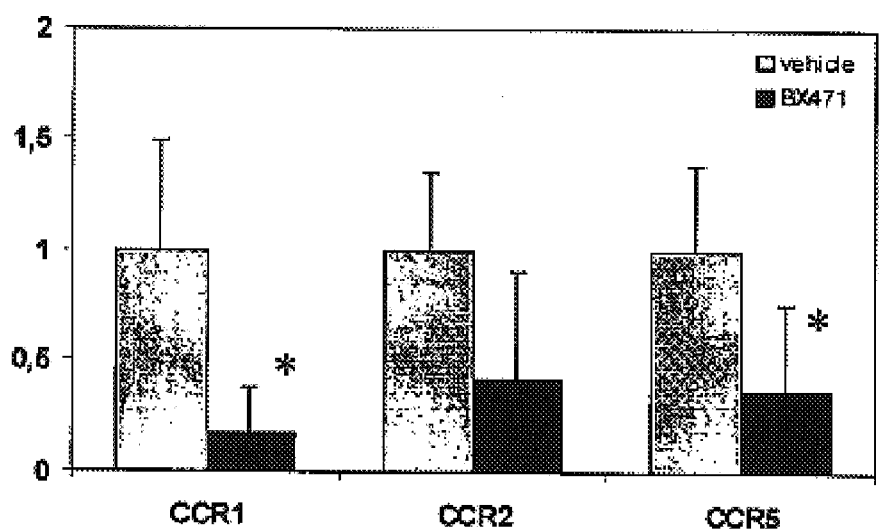

To further characterize the cellular infiltrate in the obstructed kidneys following UUO, renal chemokine receptor expression was determined by real-time quantitative RT-PCR, as described below in Example 6, the results of which are illustrated in FIG. 6. Renal CCR1, CCR2, and CCR5 mRNA expression was significantly increased in obstructed as compared to unobstructed kidneys 10 days following UUO (compare "UUO" and "CLK" in panel A in FIG. 6). Renal CCR1 (p=0.005) and CCR5 (p=0.003) mRNA expression was significantly reduced in obstructed kidneys of mice given the non-peptide CCR1 receptor antagonist BX471 for 10 days following UUO as compared to vehicle-treated animals (compare "BX471" and "Vehicle" in panel B in FIG. 6). Renal CCR2 mRNA expression was also reduced, although this decrease did not reach statistical significance (p=0.07). This data demonstrated that the non-peptide CCR1 receptor antagonist was able to substantially reduce the infiltration of chemokine receptor-expressing cells in the obstructed kidneys when given to animals for 10 days immediately following UUO.

Figure 7:
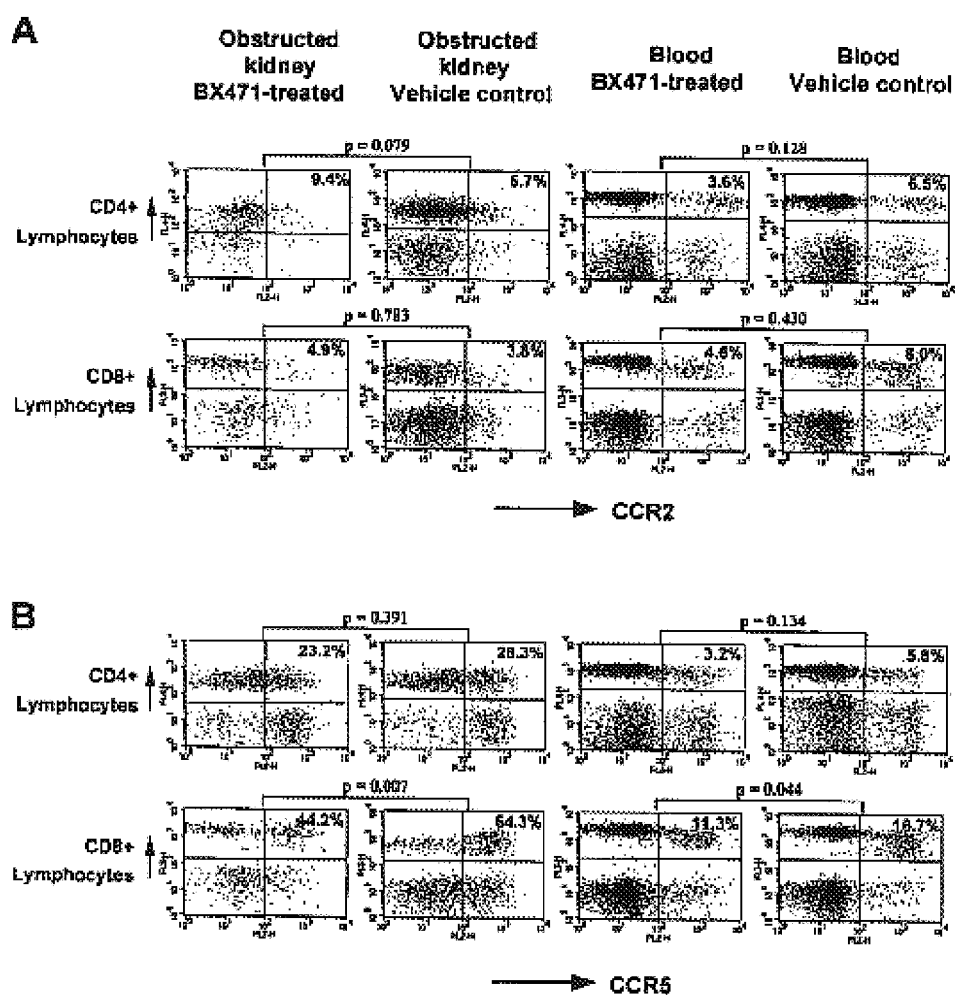
FIG. 7 shows the effect of a non-peptide CCR1 receptor antagonist of the invention on the expression of CCR2 and CCR5 on T cells isolated from the obstructed kidneys and blood of mice.

$CCR5^+$ T cells are a marker for lymphocytes that are involved in chronic inflammatory lesions. In human renal biopsies, CCR5$^+$ T cells are predominantly located in the tubulointerstitium and their presence correlates with disease activity (see Segerer, S. et al., (2001), supra). To characterize the chemokine receptor expression of the cellular infiltrate in the obstructed kidneys following UUO, flow cytometric analysis was performed on renal cell isolates, as described below in Example 7, the results of which are illustrated in FIG. 7. The number of CCR5$^+$ CD8$^+$ T cells infiltrating the obstructed kidneys of animals given vehicle (64.3%) was markedly increased as compared to the number of CCR5$^+$ CD8$^+$ T cells infiltrating the contralateral kidneys (44%, data not shown) or present in peripheral blood (16.7%) (panel B in FIG. 7). The number of CCR5$^+$ CD8$^+$ T cells infiltrating the obstructed kidneys of animals given the non-peptide CCR1 receptor antagonist BX471 (44.2%, p=0.007) was significantly reduced as compared to vehicle-treated animals. No increase in the number of CCR5$^+$ CD4$^+$ T cells, CCR2$^+$ CD4$^+$ T cells or CCR2$^+$ CD8$^+$ T cells was noted in the obstructed kidneys as compared to contralateral kidneys or peripheral blood of vehicle-treated animals, or in the obstructed kidneys of animals given vehicle as compared to the non-peptide CCR1 receptor antagonist BX471 (FIG. 7, data not shown). This data demonstrated that the non-peptide CCR1 receptor antagonist was able to reduce the infiltration of CCR5$^+$ CD8$^+$ T cells in the obstructed kidneys when given to animals for 10 days following UUO.

Figure 8:
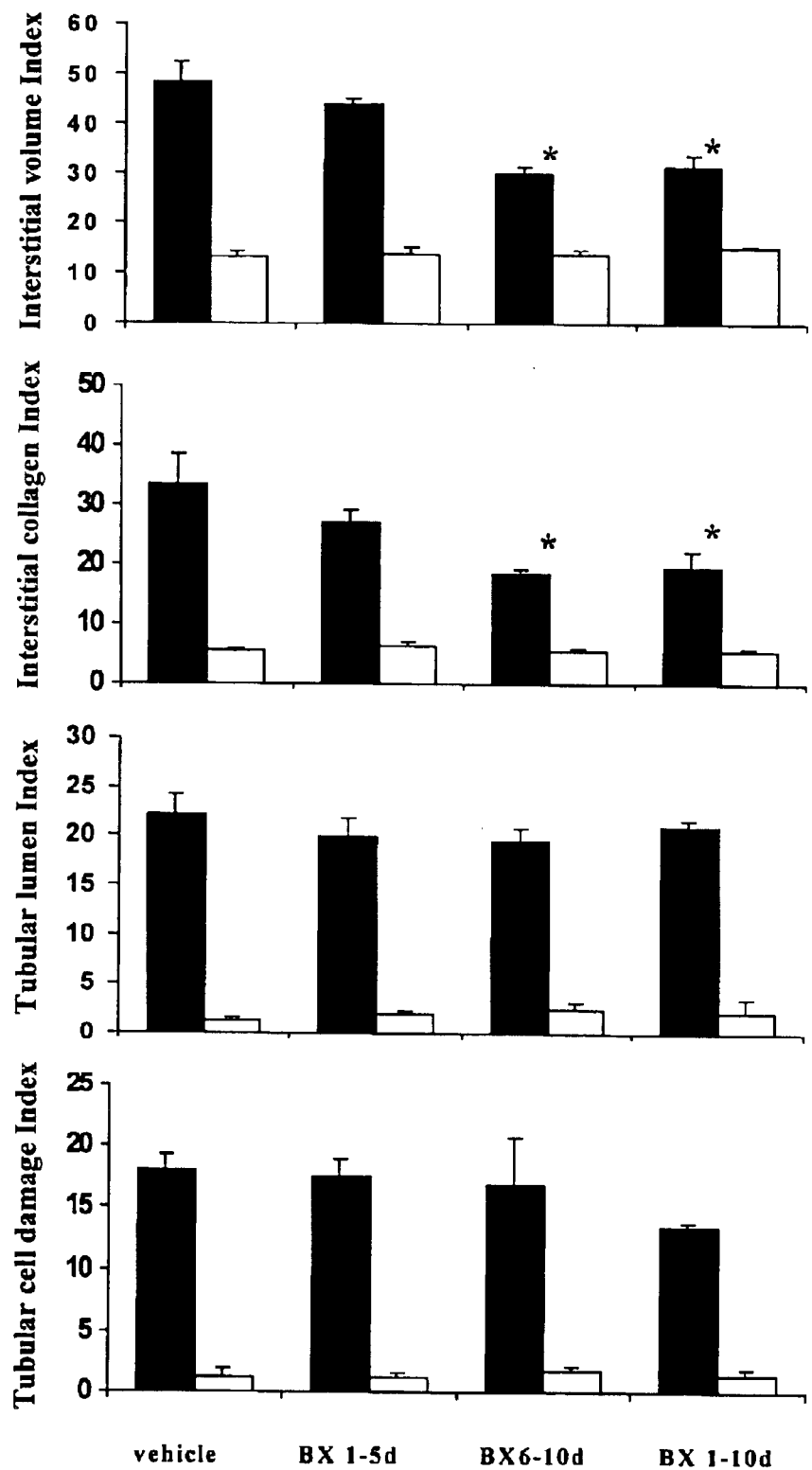
FIG. 8 shows the effect of a non-peptide CCR1 receptor antagonist of the invention on the histopathological damage to the kidneys of mice after unilateral ureteral obstruction.

To characterize the effect of the non-peptide CCR1 receptor antagonist of the invention on interstitial volume, collagen deposition, tubular lumen damage and tubular cell damage in the obstructed kidneys following UUO, morphometric analysis of silver stained renal sections was performed, as described below in Example 4, the results of which are illustrated in FIG. 5 and quantified in FIG. 8. A marked widening of the interstitial space with deposition of fibrous tissue in areas of dilatated tubuli was observed 6 and 10 days after UUO in the obstructed kidneys of animals given vehicle (panels G and H in FIG. 5). There was a marked increase in the interstitial volume, interstitial collagen, tubular lumen damage and tubular cell damage in the obstructed kidneys (black bars) as compared to the unobstructed contralateral kidneys (white bars) of animals given vehicle ("Vehicle" in FIG. 8). The interstitial volume and interstitial collagen were reduced in the obstructed kidneys of animals given the non-peptide CCR1 receptor antagonist for 10 days following UUO ("BX 1–10 d" in FIG. 8; panel J in FIG. 5) or for 5 days from days 6–10 following UUO ("BX 6–10 d" in FIG. 8; panel I in FIG. 5). There was no significant reduction in the interstitial volume or interstitial collagen in the obstructed kidneys of animals given the non-peptide CCR1 receptor antagonist for 5 days from days 1–5 following UUO ("BX 1–5 d" in FIG. 8). The parameters of tubular dilatation and tubular epithelial cell damage in the obstructed kidneys were unaffected by treatment of animals with the CCR1 receptor antagonist. These data demonstrated that the non-peptide CCR1 receptor antagonist was able to substantially reduce interstitial volume and interstitial collagen in the obstructed kidneys when given to animals for 10 days immediately following UUO or 5 days from days 6–10 following UUO.

Figure 9:
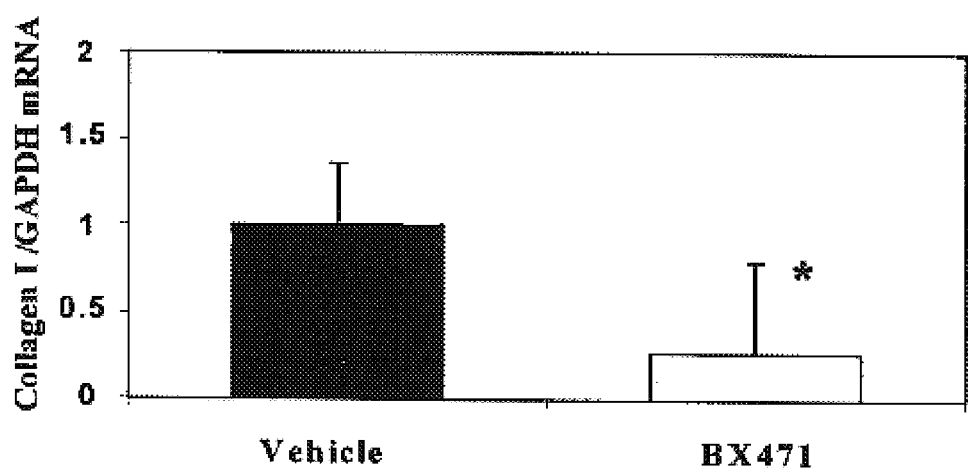
FIG. 9 shows the effect of a non-peptide CCR1 receptor antagonist of the invention on the levels of collagen I mRNA and protein in the kidneys of mice after unilateral ureteral obstruction.
Figure 9:

To further characterize the collagen deposition in the obstructed kidneys following UUO, collagen I mRNA and protein expression were assessed, as described below in Examples 6 and 8, the results of which are illustrated in FIG. 9. Renal collagen I mRNA expression was significantly reduced in obstructed kidneys of animals given the non-peptide CCR1 receptor antagonist BX471 for 10 days following UUO as compared to vehicle-treated animals (panel A in FIG. 9, p<0.05). Western blotting using a specific collagen I antibody demonstrated an increase in collagen I protein in renal extracts derived from the obstructed kidneys as compared to unobstructed contralateral kidneys of animals given vehicle (compare "UUO Vehicle" and "CLK Vehicle" in panel B in FIG. 9). Treatment of animals with the non-peptide CCR1 receptor antagonist for 10 days following UUO resulted in a decrease in collagen I protein in renal extracts derived from the obstructed kidneys (compare "UUO BX 1–10 d" and "UUO Vehicle" in FIG. 9). These data demonstrated that the non-peptide CCR1 receptor antagonist was able to substantially reduce collagen I mRNA and protein expression in the obstructed kidneys when given to animals for 10 days following UUO.

E. Administration of the Compositions of the Invention

Administration of the pharmaceutical compositions of the invention can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutical compositions will contain about 1% to about 99% by weight of the active ingredients of the compositions, i.e. the non-peptide CCR1 receptor antagonist or a pharmaceutically acceptable salt thereof and cyclosporin A, and 99% to 1% by weight of a suitable pharmaceutical excipient. Preferably, the composition will be about 5% to 75% by weight of the active ingredients, with the rest being suitable pharmaceutical excipients.

The preferred route of administration is oral, using a convenient daily dosage regimen, which can be adjusted according to the degree of severity of the rejection of the heart transplant. For such oral administration, a pharmaceutical composition of the invention is formed by the incorporation of one or more of the normally employed pharmaceutical excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such pharmaceutical compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The pharmaceutical compositions of the invention may also be formulated into a suppository using, for example, about 0.5% to about 50% active ingredients disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., the pharmaceutical compositions of the invention (about 0.5% to about 20%) and optional pharmaceutical adjuvants in a carrier, such as, for example, water, saline, aqueous dextrose, glycerol, ethanol and the like, to thereby form a solution or suspension.

If desired, pharmaceutical compositions of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods which can be used to prepare the above compositions are known, or will be apparent, to those skilled in this art; for example, see *Remington's Pharmaceutical Sciences*, 18th Ed., (Mack Publishing Company, Easton, Pa., 1990). The pharmaceutical compositions to be administered will, in any event, contain a pharmaceutically acceptable excipient and a therapeutically effective amount of a non-peptide CCR1 receptor antagonist of the invention for treatment of progressive renal fibrosis.

A therapeutically effective amount of a non-peptide CCR1 receptor antagonist, preferably a non-peptide CCR1 receptor antagonist of formula (I), will vary depending upon a variety of factors including the activity of the specific compound employed; the metabolic stability and length of action of the compound; the age, body weight, general health, sex, and diet of the patient; the mode and time of administration; the rate of excretion; the severity of the rejection process; and the host undergoing therapy. Generally, a therapeutically effective daily dose is from about 0.14 mg to about 14.3 mg/kg of body weight per day of a non-peptide CCR1 receptor antagonist of formula (I); preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of the non-peptide CCR1 receptor antagonist; preferably from about 50 mg to about 700 mg per day, and most preferably from about 100 mg to about 500 mg per day.

F. Preparation of the Compositions of the Invention

The non-peptide CCR1 receptor antagonists of the invention are prepared according to methods described in U.S. Pat. No. 6,207,665.

The following examples are provided as a guide to assist in the practice of the invention, and are not intended as a limitation on the scope of the invention.

EXAMPLE 1

In Vitro Assay

In vitro Binding Assay for Non-Peptide CCR1 Receptor Antagonists

This assay demonstrates the affinities of the non-peptide CCR1 receptor antagonists of the invention, preferably a non-peptide CCR1 receptor antagonist of formula (I), for binding to the mouse CCR1 receptor.

Reagents and Solutions:

Chemokines: MIP-1α and RANTES (Peprotech Inc.)
Cells: The 293MR (human CCR1 receptor expressing HEK 293 cells) and 293M3X (mouse CCR1 expressing HEK 293 cells) cell lines are described in Hesselgesser, J. et al., (1998), supra and Liang, M. et al., (2000a), supra. The 293M3X/pEAK10-Gqi5 cell line was generated by transfecting 293M3X cells with the plasmid pEAK-Gqi, which directs the overexpression of the chimeric G-protein Gqi5, using Lipofectamine (Life Technologies), followed by selection in puromycin (Edge BioSystems). PEAK10-Gqi5 was constructed by ligating the HinDIII/NotI fragment from plasmid pLEC-Gqi5-HA (Molecular Devices) into HinDIII/NotI digested pEAK10 (Edge BioSystems).

Ligand: $^{125}$I-MIP-1α from New England Nuclear (specific activity is 2200 Ci/mmol, 25 μCi/vial) was reconstituted in 1 mL $H_2O$.

Assay buffer: 130 mM NaCl, 5 mM KCl, 1 mM $MnCl_2$, 50 mM Tris-HCl, 30 μg/ml bacitracin, 0.1% BSA, pH 7.4.

Wash buffer: Phosphate buffer solution (PBS)

Compounds of the Invention: The stock solution of the compounds was 1 mM in 100% DMSO. The highest concentration in the assay was 10 μM and may vary depending on the potency of the compounds. Serial 1:3 dilutions from the highest concentration were made with assay buffer. Six concentrations of each compound were typically screened to generate a dose curve from which the $K_i$ value was determined.

Assay Procedure:

Assays were performed in 96-well v-bottom microtiter plates in a total volume of 100 μL.

HEK 293 cells stably expressing human (293MR) or mouse (293M3X) CCR1 receptor were grown to confluent monolayers in T-225 $cm^2$ flasks. Cells were washed once in PBS and resuspended in the assay buffer to about 0.2 to $1.0 \times 10^6$ cells/mL. Cells were incubated with $^{125}$I-MIP-1α in the presence or absence of varying concentrations of unlabeled MIP-1α or compound at 4° C. for 30 minutes.

The reactions were terminated by removing aliquots from the cell suspension and separating cells from buffer by centrifugation through a silicon/paraffin oil mixture as described in Hesselgesser, J. et al., (1998), supra and Liang, M. et al., (2000a), supra.

The nonspecific binding was determined in the presence of 100 nM or 1 μM of unlabeled MIP-1α. The concentrations of compounds in the assay were typically from 10 μM to 30 nM in 1:3 dilutions and the concentrations for more potent compounds were lower depending on the potency.

Calculations:

The dose curves of each compound with 6 concentration points were generated and the binding data were curve fitted with the computer program IGOR (Wavemetrics) to determine the affinity and number of sites.

The non-peptide CCR1 receptor antagonists of the invention, when tested in this assay, demonstrated their affinity to bind to the mouse CCR1 receptor.

EXAMPLE 2

In Vitro Assay: Calcium Flux

Functional in vitro Assay for Non-Peptide CCR1 Receptor Antagonists

Since the CCR1 receptor responds to the binding of its ligands, MIP-1α and RANTES, by mobilizing free intracellular calcium, one can measure biological activity by calcium flux assays using the fluorescent dye flou-3. In the following assay the ability of the non-peptide CCR1 receptor antagonists of the invention to block this biologic response was measured.

Protocol:

1) 293MR and 293M3XpEAK10-Gqi5 cells were grown as described in Example 1. Cells were lifted from flasks using an enzyme-free, PBS-based dissociation buffer (Life Technologies).

2) Cells were loaded with fluo-3 by resuspension at 1 to 2×10⁶ cells/mL in HanksBSS (Life Technologies), 20 mM Hepes, 3.2 mM $CaCl_2$, 1% heat-inactivated fetal bovine serum, 2.5 mM probenecid, 0.04% Pluronic F-127, 4 μM fluo-3, pH 7.4, and incubated at 37° C. for 1 to 1.5 hours.

2) Following incubation, the cells were pelleted by centrifugation and resuspended at a density of 1×10⁶ cells/mL in HanksBSS, 20 mM Hepes, 1 mM $CaCl_2$, 1% heat-inactivated fetal bovine serum, 2.5 mM probenecid, pH 7.4 and kept at 37° C. for analysis.

3) Fluo-3 loaded cells were preincubated at 37° C. for 15 minutes in the presence or absence of various concentrations of the non-peptide CCR1 receptor antagonists of the invention.

4) Cells were stimulated with 10 nM MIP-1α (Peprotech Inc.) and $Ca^{2+}$ release was measured as a function of time in a PTO Deltascan Model 4000 spectrofluorimeter running FeliX version 1.41 (Photon Technologies International).

5) The data were corrected for nM $Ca^{2+}$ released by adding 100 μL of 0.1% Triton X-100 (for maximum values) followed by 100 μL of 500 mM EGTA, pH 8.5 (for minimum values).

The non-peptide CCR1 receptor antagonists of the invention, when tested in this assay, demonstrated their ability to inhibit $Ca^{2+}$ mobilization in response to the binding of MIP-1α to the mouse CCR1 receptor.

EXAMPLE 3

In Vivo Assay

Pharmacokinetic Studies in Mice

Conscious adult, male C57BL/6 mice (Charles River) 12+/−2 weeks of age were used in these studies.

A solution of 40% cyclodextrin was prepared by adding Cyclodextrin (400 g, Sigma-Aldrich) into a 1 liter sterile plastic bottle. Unbuffered saline was added and the mixture was mixed overnight to dissolve. Saline was added to a total volume of 1 liter. The solution was filtered through a 0.45 μm filter into a sterile bottle, labeled and stored at 4° C. A 20 mg/ml solution, pH 3.3, of compound in cyclodextrin was prepared by dissolving the compound into the 40% cyclodextrin in saline. The mixture was stirred to dissolve. After dissolution was complete, the pH of the solution was raised to 4.5 by addition of 1 M KOH. The solution was filtered through a 0.45 μm filter and stored at 4° C.

The non-peptide CCR1 receptor antagonists of the invention were prepared in a vehicle of 40% cyclodextrin/saline, and mice were subcutaneously (s.c.) dosed (single injection at 20 mg/kg). Blood samples were collected by cardiac puncture in EDTA-containing tubes at various times, centrifuged and plasma was stored frozen until analyzed for drug levels.

Plasma samples were analyzed either by HPLC using UV detection methods or HPLC-MS (electrospray mode operated under a positive ion mode). Concentrations of the non-peptide CCR1 receptor antagonists of the invention were determined through a calibration curve constructed in plasma and analyzed under identical conditions. Related compounds were used as internal standards in these analyses.

HPLC-UV Method:

1) 100 μL aliquots of plasma samples were added to 200 μL ice cold acidic methanol (1% acetic acid) containing a fixed amount of an internal standard and mixed well.

2) The resulting protein precipitate was removed by centrifugation at 5,000×g and the supernatents were collected.

3) In parallel, control plasma samples were spiked with various amounts of the non-peptide CCR1 receptor antagonists of the invention, typically in the range of 0.3 to 25 μM, and processed as above.

4) The supernatents were evaporated to dryness in a vacuum evaporator, reconstituted with a 1:2 methanol: water solution (containing 0.1% TFA), vortexed for 30 sec and centrifuged to remove sediments.

5) The resulting supernatents were injected onto a YMC AQ ODS reversed phase column and analyzed under gradient HPLC conditions at a flow rate of 1 mL/min. The UV detector was set at 230 nm.

6) The gradient conditions were: initial, solvent A 22%/solvent B 78%; 2 min, solvent A 22%/solvent B 78%; 33 min solvent A 45%/solvent B55%; 37 min solvent A 80%/solvent B 20%; 47 min solvent A 80%/solvent B 20%; 49 min, back to initial conditions.

7) Peak area ratios between the internal standard peak and the compound were calculated over the concentration range of the standard curve and this ratio was used to construct a calibration curve. The concentration of the compound of interest was derived from this curve by calculating the peak area ratio between the compound and internal standard peaks.

HPLC-MS Method:

1) The methodology used was similar to that described above, except that the sample preparation was stopped at the methanol precipitation step, and a short isocratic method was used instead of the gradient method.

2) A FISONS VG Platform single quadrupole instrument was used with an electrospray inlet operated at 3.57 kV. A YMC AQ ODS reversed phase column was employed under a flow rate of 1 mL/min with the total flow going into the UV detector at 214 nm.

3) The flow was split to infuse 50 μL/min into the mass spectrometer. Chromatograms were collected over a total run time of 7.5 min per sample with a 50 μL injection on the column. The ions were collected in a single ion positive ionization mode.

4) Quantitation was accomplished by integrating the area under the ion currents (control non-peptide CCR1 receptor antagonist of the invention and internal standards) and generating a calibration curve as described above.

The non-peptide CCR1 receptor antagonists of the invention, when tested in this assay, demonstrated adequate drug levels in mouse plasma over a 8 hour period when given subcutaneously at 20 mg/kg.

EXAMPLE 4

In Vivo Assay

Unilateral Ureteral Obstruction in C57BL/6 Mice

Adult male, C57BL/6 mice (Charles River) 12+/−2 weeks of age were used in these studies.

Unilateral ureteral obstruction ("UUO") was performed under general ether anesthesia by ligating the left ureter with 2/0 Mersiline through a midline abdominal incision. All mice were sacrificed 10 days after UUO by cervical dislocation under general anesthesia with inhaled ether. Contralateral kidneys served as intraindividual controls.

Group I ("Vehicle"): Control mice were treated subcutaneously with 50 µL of vehicle (40% cyclodextrin in saline) for 10 days at 8 hour intervals beginning immediately after UUO.

Group II ("BX 1–5 d"): Mice were treated with 20 mg/kg BX471 in 50 µL of vehicle for 5 days at 8 hour intervals beginning immediately after UUO.

Group III ("BX 6–10 d"): Mice were treated with 20 mg/kg BX471 in 50 µL of vehicle for 5 days at 8 hour intervals beginning on day 6 after UUO.

Group IV ("BX 1–10 d"): Mice were treated with 20 mg/kg BX471 in 50 µL of vehicle for 10 days at 8 hour intervals beginning immediately after UUO.

From each mouse, the obstructed and unobstructed contralateral kidneys were divided vertically into two halves by a midline cut. The lower half was fixed in 4% formalin in PBS and embedded in paraffin. Two µm sections were stained with periodic acid-Schiff reagent and silver using a commercial kit following the supplier's instructions (Bio-Optica). To count interstitial cells, 12 high power fields (hpf, 400×) were analyzed by a blinded observer. Positive cells were counted per high power field, omitting positive cells in glomerular or direct periglomerular fields. Subcapsular fields (up to 50 µm) were not evaluated to avoid stain-related edge artifacts.

Quantification of the interstitial volume was performed as described in Vielhauer, V. et al., (2001), supra. The interstitial volume index ($I_{int}$) was determined by superimposing a grid containing 100 (10×10) sampling points on photographs of 12 non-overlapping cortical fields of silver-stained tissue (hpf, 400×) of each kidney. The number of points overlying interstitial space was counted, while points falling on glomerular, vascular or tubular structures were excluded from the count and related to the number of all 100 points. The amount of collagen deposition ($I_{col}$) was expressed by the amount of points overlying interstitial collagen. Points overlying tubular basement membranes, Bowman's capsule or perivascular tissue were not counted.

Tubular cell damage was also quantified by the above method. For the tubular cell damage index ($I_{TCD}$) the number of points overlying flattened or necrotic tubular cells was counted and related to the number of all points. Points falling on glomerular, vascular or normal tubular structures, as well as tubular lamina, were excluded from the count. The tubular dilatation index ($I_{Tdil}$) was similarly assessed, by counting the number of points overlying tubular lamina.

The non-peptide CCR1 receptor antagonists of the invention, when tested in this assay, demonstrated the ability to reduce leukocyte infiltration, fibroblast activation, interstitial volume and collagen deposition in the peritubular interstitium in the obstructed kidneys after UUO.

EXAMPLE 5

In Vivo Assay

Immunohistochemistry

All immunological studies were performed on paraffin-embedded sections, which were deparrafinized, microwave-treated for 5 minutes, and blocked with 3% peroxidase, avidin and biotin (Vector Blocking Kit, Vector Laboratories) for 20 minutes. After washing with PBS, slices were incubated with the primary antibody at ambient temperature for 1 hour. The following rat and rabbit antibodies were used as primary antibodies: 1:100 rat anti-mCD45 (leukocytes, Pharmingen); 1:50 rat anti-F4/80 (macrophages, Serotec); 1:50 rat anti-CD3 (lymphocytes, Serotec); and 1:500 rat anti-FSP1 (activated fibroblasts, Dr. F. Strutz, Göttingen, Germany). Signals were detected with a commercial mouse link and label kit following the supplier's instructions (Biogenix SuperSensitive). 3-amino-9-ethylcarbazole-1 substrate was used for signal development. All stains were counter-stained with hemalaun (Sigma-Aldrich).

The non-peptide CCR1 receptor antagonists of the invention, when tested in this assay, demonstrated the ability to reduce leukocyte infiltration and fibroblast activation in the peritubular interstitium in the obstructed kidneys after UUO.

EXAMPLE 6

In Vivo Assay

Chemokine Receptor and Collagen I mRNA Expression

From each mouse, a specimen of both kidneys was snap frozen in liquid nitrogen and stored at −80° C. Total RNA was prepared as described in Chomczynski, P. and Sacci, N., Anal. Biochem. (1987), Vol. 162, pp. 156–159. The RNA pellet was air-dried, dissolved in DEPC-treated water, and stored at −80° C. One µg of total RNA was subjected to random-primed (Hexamer, Roche) reverse transcription at 42° C. for 1 hour using a modified MMLV reverse transcriptase (Superscript, Life Technologies). Real time RT-PCR was performed on a TaqMan ABI 7700 Sequence Detection System (PE Biosystems) using a heat-activated Taq DNA polymerase (Amplitaq Gold, PE Biosystems). Thermal cycler conditions contained holds at 50° C. for 2 minutes and 95° C. for 10 minutes followed by 40 cycles of 95° C. for 15 seconds and 60° C. for 60 seconds. GAPDH was used as reference gene. The following oligonucleotide primers (300 nM) and probes (100 nM) (PE Biosystems) were used: (a) murine collagen 1α1 (gb X54876; bp 1984–2102); forward primer: 5'-TGCTTTCTGCCCGGAAGA-3' (SEQ ID NO: 1); reverse primer: 5'-GGGATGCCATCTCGTCCA-3' (SEQ ID NO: 2); internal fluorescence labeled probe (FAM): 5'-CCAGGGTCTCCCTTGGGTCCTACATCT-3' (SEQ ID NO: 3); (b) murine GAPDH (gb M32599, bp 730–836); forward primer: 5'-CATGGCCTTCCGTGTTCCTA-3' (SEQ ID NO: 4); reverse primer: 5'-ATGCCTGCTTCACCACCTTCT-3' (SEQ ID NO: 5); internal fluorescence labeled probe (VIC): 5'-CCCAATGTGTCCGTCGTGGATCTGA-3' (SEQ ID NO: 6); (c) murine CCR1 (gb NM_009912, bp 487–586); forward primer: 5'-TTAGCTTCCATGCCTGCCTTATA-3' (SEQ ID NO: 7); reverse primer: 5'-TCCACTGCTTCAGGCTCTTGT-3' (SEQ ID NO: 8); internal fluorescence labeled probe (T1): 5'-ACTCACCGTACCTGTAGCCCTCATTTCCC-3' (SEQ ID NO: 9); (d) murine CCR2 (gb NM_009915, bp 984–1095); forward primer: 5'-CCTTGGGAATGAGTAACTGTGTGA-3' (SEQ ID NO: 10); reverse primer: 5'-ACAAAGGCATAAATGACAGGATTAATG-3' (SEQ ID NO: 11); internal fluorescence labeled probe (T1, FAM): 5'-TGACAAGCACTTAGACCAGGCCATGCA-3' (SEQ ID NO: 12); and (e) murine CCR5 (gb D83648, bp 1065–1191); forward primer: 5'-CAAGACAATCCTGATCGTGCAA-3' (SEQ ID NO: 13); reverse primer: 5'-TCCTACTCCCAAGCTGCATAGAA-3' (SEQ ID NO: 14); internal fluorescence labeled probe (T1, FAM): 5'-TCTATACCCGATCCACAGGAGAACATGAAGTTT-3' (SEQ ID NO: 15).

EXAMPLE 7

In Vivo Assay

Flow Cytometry

A preparation of renal cells including infiltrating leukocytes was obtained from obstructed and contralateral kidneys as described (Vielhauer, V. et al., (2001), supra). Mechanically disaggregated tissue was digested with collagenase type I and deoxyribonuclease type III (both from Sigma-Aldrich) at 37° C. The resulting supernatant and blood samples taken from anesthetized mice by retrobulbar puncture were then labeled for flow cytometry. Renal cell suspensions and full blood samples in EDTA were incubated with 5 µg/mL of rat monoclonal antibodies against mouse CCR2 or CCR5 or with isotype control rat IgG2b (Pharmingen) on ice for 60 minutes. After washing, the cells were incubated with a biotin-labeled anti-rat polyclonal antibody followed by phycoerythrin-labeled streptavidin (both from Dako). To identify leukocyte subsets, samples were finally incubated with a combination of the following directly conjugated cell-specific antibodies: CD11b fluorescein-isothiocyanate (clone M1/70), CD4 allophycocyanin, and CD8 Cy-chrome (all from Pharmingen). After lysis of erythrocytes with FACS-lysing solution (Becton-Dickenson), stained cells were analyzed on a flow cytometer (FACScalibur, Becton-Dickenson). Monocytes/macrophages were identified by their light scatter properties and expression of CD11b, and T lymphocytes were identified by expression of CD4 or CD8. The cut-off to define chemokine receptor positive cells was set according to the staining with the isotype control antibody. Approximately 100,000 gated events were collected in each analysis.

The non-peptide CCR1 receptor antagonists of the invention, when tested in this assay, demonstrated the ability to reduce infiltration of CCR5$^+$ CD8$^+$ T cells in the obstructed kidneys after UUO.

EXAMPLE 8

In Vivo Assay

Collagen I Protein Expression

From each mouse, a specimen of both kidneys was snap frozen in liquid nitrogen and stored at −80° C. Kidneys were homogenized in RIPA buffer (50 mM Tris-HCl, pH 8.0, 1% Nonidet P40, 0.5% sodium deoxycholate, 150 mM NaCl, 0.1% SDS, complete Protease-inhibitor tablet (Roche)). Extracted proteins were boiled in loading buffer for 10 minutes, resolved by 8% SDS-PAGE under reducing conditions and transferred to an Immobilon-P membrane (Millipore). After blocking, the filter was incubated with the rabbit polyclonal anti-collagen I antibody (1:1000 in blocking solution, Chemicon) and immune complexes were visualized using horseradish peroxidase-conjugated goat anti-rabbit antibody (1:5000 in blocking solution, Jackson ImmunoResearch) and then processed for detection by enhanced chemiluminescence (ECL, Amersham Pharmacia).

The non-peptide CCR1 receptor antagonists of the invention, when tested in this assay, demonstrated the ability to reduce the expression of collagen I protein in the obstructed kidneys after UUO.

EXAMPLE 9

This example illustrates the preparation of representative pharmaceutical compositions of the invention for oral administration:

| A. | Ingredients | % wt./wt. |
|---|---|---|
| | Active ingredients | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Active ingredients | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Active ingredients | 0.1 g |
| | Propylene glycol | 20.0 g |
| | Polyethylene glycol 400 | 20.0 g |
| | Polysorbate 80 | 1.0 g |
| | Water | q.s. 100 mL |

The active ingredients are dissolved in propylene glycol, polyethylene glycol 400 and polysorbate 80. A sufficient quantity of water is then added with stirring to provide 100 mL of the solution, which is filtered and bottled.

| D. | Ingredients | % wt./wt. |
|---|---|---|
| | Active ingredients | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Active ingredients | 1.0% |
| | Methyl or carboxymethyl cellulose | 2.0% |
| | 0.9% saline | q.s. 100 mL |

The active ingredients are dissolved in the cellulose/saline solution, filtered and bottled for use.

EXAMPLE 10

This example illustrates the preparation of a representative pharmaceutical composition of the invention for parenteral administration:

| Ingredients | |
|---|---|
| Active ingredients | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The active ingredients are dissolved in propylene glycol, polyethylene glycol 400 and polysorbate 80. A sufficient quantity of 0.9% saline solution is then added with stirring to provide 100 mL of the I.V. solution, which is filtered through a 0.2 μm membrane filter and packaged under sterile conditions.

EXAMPLE 11

This example illustrates the preparation of a representative pharmaceutical composition of the invention in suppository form:

| Ingredients | % wt./wt. |
|---|---|
| Active ingredients | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 12

This example illustrates the preparation of a representative pharmaceutical composition of the invention for insufflation:

| Ingredients | % wt./wt. |
|---|---|
| Micronized active ingredients | 1.0% |
| Micronized lactose | 99.0% |

The ingredients are milled, mixed, and packaged in an insufflator equipped with a dosing pump.

EXAMPLE 13

This example illustrates the preparation of a representative pharmaceutical composition of the invention in nebulized form:

| Ingredients | % wt./wt. |
|---|---|
| Active ingredients | 0.005% |
| Water | 89.995% |
| Ethanol | 10.000% |

The active ingredients are dissolved in ethanol and blended with water. The formulation is then packaged in a nebulizer equipped with a dosing pump.

EXAMPLE 14

This example illustrates the preparation of a representative pharmaceutical composition of the invention in aerosol form:

| Ingredients | % wt./wt. |
|---|---|
| Active ingredients | 0.10% |
| Propellant 11/12 | 98.90% |
| Oleic acid | 1.00% |

The active ingredients are dispersed in oleic acid and the propellants. The resulting mixture is then poured into an aerosol container fitted with a metering valve.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating progressive renal fibrosis in a mammal which method comprises administering to a mammal in need thereof a pharmaceutical composition comprising a pharmaceutically acceptable excipient and a therapeutically effective amount of a non-peptide CCR1 receptor antagonist, wherein the non-peptide CCR1 receptor antagonist is a compound selected from formula (I):

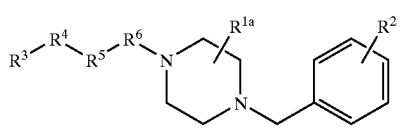

wherein
- $R^{1a}$ is one or more substituents independently selected from the group consisting of alkyl and hydroxyalkyl;
- $R^2$ is fluoro at the 4-position;
- $R^3$ is phenyl substituted at the 4-position with chloro and at the 2-position by aminocarbonyl, ureido or glycinamido;
- $R^4$ is —O—;
- $R^5$ is methylene; and
- $R^6$ is —C(O)—, a single stereoisomer or a mixture thereof; or a pharmaceutically acceptable salt thereof.

2. The method of claim 1 wherein the non-peptide CCR1 receptor antagonist is selected from the group consisting of:

(2R,5S)-1-((4-chloro-2-(aminocarbonyl)phenoxy)methyl)carbonyl-2,5-dimethyl-4-(4-fluorobenzyl)piperazine;

(trans)-1-((4-chloro-2-(glycinamido)phenoxy)methyl)carbonyl-2,5-dimethyl-4-(4-fluorobenzyl)piperazine;

(2R)-1-((4-chloro-2-(ureido)phenoxy)methyl)carbonyl-2-methyl-4-(4-fluorobenzyl)piperazine;

(trans)-1-((4-chloro-2-(ureido)phenoxy)methyl)carbonyl-2,5-dimethyl-4-(4-fluorobenzyl)piperazine;

(2R,5S)-1-((4-chloro-2-(ureido)phenoxy)methyl)carbonyl-2,5-dimethyl-4-(4-fluorobenzyl)piperazine; and (2R,5S)-1-((4-chloro-2-(glycinamido)phenoxy)methyl)carbonyl-2,5-dimethyl-4-(4-fluorobenzyl)piperazine.

3. The method of claim 1 wherein the non-peptide CCR1 receptor antagonist is (2R)-1-((4-chloro-2-(ureido)phenoxy)methyl)carbonyl-2-methyl-4-(4-fluorobenzyl)piperazine.

4. The method of claim 3 wherein the mammal in need thereof is a human.

* * * * *

SEQUENCE LISTING

<160> NUMBER OF SEQ ID NOS: 15

<210> SEQ ID NO 1
<211> LENGTH: 18
<212> TYPE: DNA
<213> ORGANISM: Homo sapiens

<400> SEQUENCE: 1 gctttctgc ccggaaga                                                      18

<210> SEQ ID NO 2
<211> LENGTH: 18
<212> TYPE: DNA
<213> ORGANISM: Homo sapiens

<400> SEQUENCE: 2
gggatgccat ctcgtcca                                                     18

<210> SEQ ID NO 3
<211> LENGTH: 27
<212> TYPE: DNA
<213> ORGANISM: Homo sapiens

<400> SEQUENCE: 3
ccagggtctc ccttgggtcc tacatct                                           27

<210> SEQ ID NO 4
<211> LENGTH: 20
<212> TYPE: DNA
<213> ORGANISM: Homo sapiens

<400> SEQUENCE: 4
catggccttc cgtgttccta                                                   20

<210> SEQ ID NO 5
<211> LENGTH: 21
<212> TYPE: DNA
<213> ORGANISM: Homo sapiens

<400> SEQUENCE: 5
atgcctgctt caccaccttc t                                                 21

<210> SEQ ID NO 6
<211> LENGTH: 25
<212> TYPE: DNA
<213> ORGANISM: Homo sapiens

<400> SEQUENCE: 6
cccaatgtgt ccgtcgtgga tctga                                             25

<210> SEQ ID NO 7
<211> LENGTH: 23
<212> TYPE: DNA
<213> ORGANISM: Homo sapiens

<400> SEQUENCE: 7
ttagcttcca tgcctgcctt ata                                               23

<210> SEQ ID NO 8
<211> LENGTH: 21
<212> TYPE: DNA
<213> ORGANISM: Homo sapiens

-continued

```
<400> SEQUENCE: 8
tccactgctt caggctcttg t                                            21

<210> SEQ ID NO 9
<211> LENGTH: 29
<212> TYPE: DNA
<213> ORGANISM: Homo sapiens

<400> SEQUENCE: 9
actcaccgta cctgtagccc tcatttccc                                    29

<210> SEQ ID NO 10
<211> LENGTH: 24
<212> TYPE: DNA
<213> ORGANISM: Homo sapiens

<400> SEQUENCE: 10
ccttgggaat gagtaactgt gtga                                         24

<210> SEQ ID NO 11
<211> LENGTH: 27
<212> TYPE: DNA
<213> ORGANISM: Homo sapiens

<400> SEQUENCE: 11
acaaaggcat aaatgacagg attaatg                                      27

<210> SEQ ID NO 12
<211> LENGTH: 27
<212> TYPE: DNA
<213> ORGANISM: Homo sapiens

<400> SEQUENCE: 12
tgaccagcac ttagaccagg ccatgca                                      27

<210> SEQ ID NO 13
<211> LENGTH: 22
<212> TYPE: DNA
<213> ORGANISM: Homo sapiens

<400> SEQUENCE: 13
caagacaatc ctgatcgtgc aa                                           22

<210> SEQ ID NO 14
<211> LENGTH: 23
<212> TYPE: DNA
<213> ORGANISM: Homo sapiens

<400> SEQUENCE: 14
tcctactccc aagctgcata gaa                                          23

<210> SEQ ID NO 15
<211> LENGTH: 33
<212> TYPE: DNA
<213> ORGANISM: Homo sapiens

<400> SEQUENCE: 15
tctatacccg atccacagga gaacatgaag ttt                               33
```